United States Patent [19]
LeFevre

[11] 4,378,013
[45] Mar. 29, 1983

[54] FLOW CONTROLLER FOR IV CHAMBER
[75] Inventor: Robert J. LeFevre, Bethlehem, Pa.
[73] Assignee: Burron Medical Inc., Bethlehem, Pa.
[21] Appl. No.: 189,906
[22] Filed: Sep. 23, 1980
[51] Int. Cl.³ .............................................. A61M 5/00
[52] U.S. Cl. .................................... 128/214 R; 251/7
[58] Field of Search ............... 128/214 R, 214 C, 274; 251/4, 7, 125

[56] References Cited
U.S. PATENT DOCUMENTS

| | | | |
|---|---|---|---|
| 2,197,995 | 4/1940 | Crowley | 251/7 |
| 2,797,837 | 7/1957 | Roberts | 251/7 X |
| 3,323,774 | 6/1967 | Wilson | 251/125 |
| 3,785,378 | 1/1974 | Stewart | 128/214 C |
| 3,920,215 | 11/1975 | Knauf | 251/7 |
| 3,977,400 | 8/1976 | Moorehead | 128/214.4 |

FOREIGN PATENT DOCUMENTS

| | | | |
|---|---|---|---|
| 960889 | 4/1950 | France | 251/7 |
| 7308538 | 12/1974 | Netherlands | 251/7 |

*Primary Examiner*—Dalton L. Truluck
*Attorney, Agent, or Firm*—Shoemaker and Mattare, Ltd.

[57] ABSTRACT

An IV chamber flow controller includes a plug integrally connected to the chamber and a flexible tube extending through the plug. A plunger rod is moved by a skirt which is rotatably mounted on the chamber and pinches off the tube to stop flow from the chamber. The skirt includes a crescent shaped groove for controlling movement of the plunger rod. A flow path from the IV chamber to an IV tube is straight and uninterrupted so that leakage and sterility problems are reduced.

3 Claims, 5 Drawing Figures

FIG. 1.
FIG. 2.
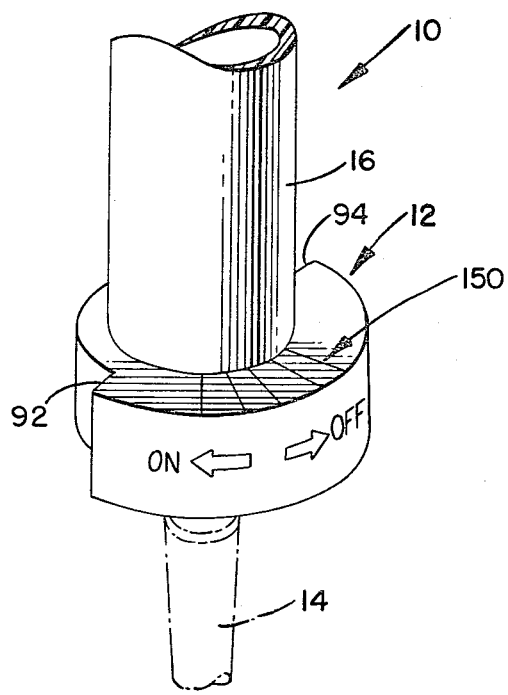
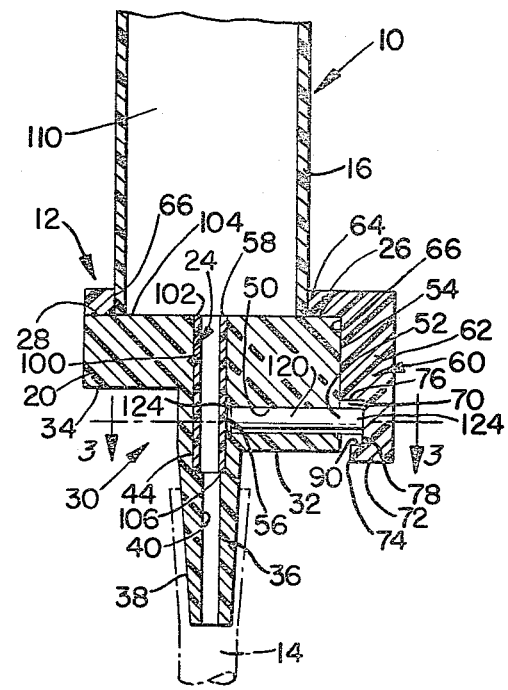
FIG. 3.
FIG. 4.
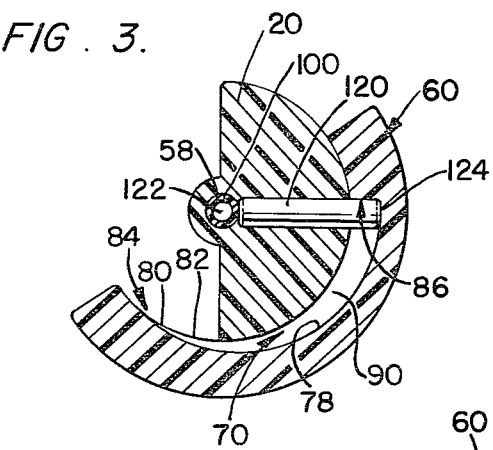
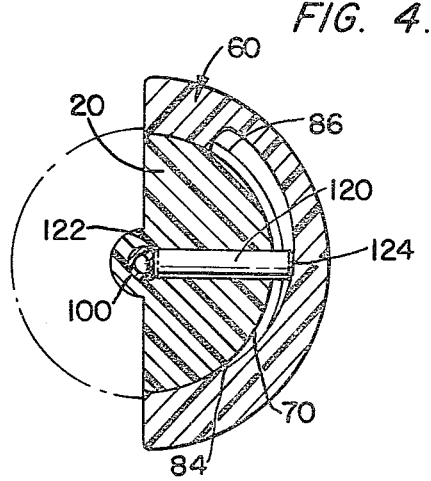
FIG. 5.
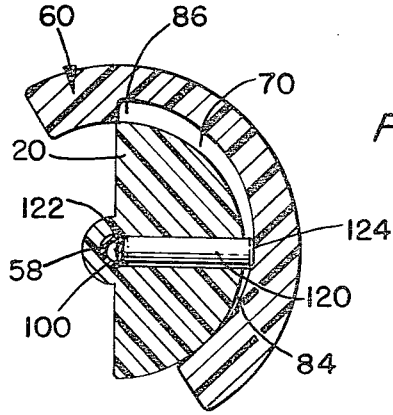

FLOW CONTROLLER FOR IV CHAMBER

BACKGROUND OF THE INVENTION

The present invention relates in general to IV equipment, and, more particularly, to flow rate controls for IV equipment.

Accurate control of the flow rate of fluids being administered to a patient is of critical importance. There are several devices which control such flow rate, with the devices disclosed in U.S. Pat. Nos. 3,323,774 and 3,785,378 being examples of such devices.

However, these known devices have sliding joints and broken fluid paths which create fluid leakage and sterility problems. Air leakage problems may also arise.

SUMMARY OF THE INVENTION

The device embodying the teachings of the present invention controls fluid flow from an IV chamber without sliding joints and broken fluid paths.

The device includes an annular plug integral with an IV chamber. The plug has a bore defined centrally thereof and has an IV tube connector depending therefrom. The tube connector has a bore defined therein to be fluidly connected to the plug bore. A flexible, deformable tube is located within the two bores.

A plunger rod bore is defined in the plug to extend radially of that plug from the plug bore to the outer surface of that plug. A plunger rod is slidably positioned in the radial bore and extends out of the plug.

A skirt surrounds the plug and has a crescent-shaped groove defined circumferentially therein to be aligned with the radial bore. The skirt is movable circumferentially of the IV chamber, and such movement alters the distance between the radial bore and the inner surface of the skirt due to the crescent-shaped groove.

As the skirt is rotated with respect to the chamber, the rod is pushed into or allowed to move outwardly of the radial bore under the influence of the natural resiliency of the tubing.

Flow rate of fluid to the IV tubing is adjusted by the amount the tubing is pinched off by the plunger rod. Such adjustment varies from zero occlusion and full flow when the rod is fully withdrawn into the radial bore, to full occlusion and zero flow when the rod is fully inserted into the axial bore, thereby completely pinching off the tubing.

There are no sliding joints and no breaks in the fluid path between the IV chamber and the IV tubing. Thus, there are no joint engendered leakage or sterility problems. Furthermore, there is no chance for air to leak into the fluid path via a joint.

OBJECT OF THE INVENTION

It is a main object of the present invention to control flow from an IV chamber while still having an unbroken fluid path from the IV chamber to the IV tubing.

This together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 1 is a perspective showing the flow control mechanism embodying the teachings of the present invention.

FIG. 2 is a cutaway elevation of the flow control mechanism embodying the teachings of the present invention.

FIG. 3 is a view taken along line 3—3 of FIG. 2 showing the device in a full open position.

FIG. 4 is a view similar to FIG. 3 showing the device in a mid-flow position.

FIG. 5 is a view similar to FIG. 3 showing the device in a zero flow, or flow-off, position.

DETAILED DESCRIPTION OF THE INVENTION

Shown in FIG. 1 is an IV chamber 10 having a drip rate control mechanism 12 integral therewith. The IV chamber receives fluid, such as parenteral fluid, or the like, from a source (not shown) and transfers that fluid to IV tubing 14 for transfer to a device administering that fluid to a patient. The chamber 10 is cylindrical and has a wall 16.

As best shown in FIG. 2, the drip rate control mechanism 12 includes a cylindrical plug 20 integral with the bottom rim of the wall 16. The plug 20 includes a bore 24 defined centrally therethrough. The plug has an outer diameter greater than the outer diameter of the wall 16 and thus has an annular shoulder 26 defined on upper surface 28 thereof. The plug has a stepped lower surface 30 which includes first surface 32 and second surface 34. A lug 36 depends from the plug and has an outer surface 38 tapered to frictionally retain IV tubing 14 thereon, and a bore 40 defined longitudinally through the lug to be aligned with and in fluid communication with bore 24. The bore 40 has an inner diameter slightly smaller than the inner diameter of the bore 24 so a shoulder 44 is defined subjacent the plane containing the first surface 32.

A bore 50 is defined radially in the plug to have one end 52 thereof defined in circumferential outer surface 54 of the plug, and the other end 56 thereof defined in inner surface 58 of the bore 24 so that the bore 24 is in communication with the outside of the plug.

A semi-cylindrical skirt 60 is rotatably mounted around the IV chamber. The skirt has a body 62 with a top 64 having a bore 66 defined therein to accommodate the chamber 10. The top 64 thus forms an annular collar surrounding the chamber. The body 62 has an inner surface 66 slidingly contacting the plug outer surface and has a groove 70 defined therein to be co-level with the bore 50. A lower rim 72 has a foot 74 which defines a lower wall of the groove 70. The groove 70 has a top wall 76 and a rear wall 78, with the rear wall 78 being located in a plane which is parallel with the plane containing the end 56 of the bore 50.

The groove 70 is best shown in FIGS. 3–5 to be crescent-shaped with a first inner surface 80 and a second inner surface 82 corresponding to rear wall 78. The surfaces 80 and 82 are located closely adjacent each other at end 84 of the groove and are spaced apart from each other at end 86 of the groove so that the groove is circumferentially narrowing in one direction and circumferentially widening in the other direction. The foot 74 has an upper surface 90 shown in FIGS. 2 and 3 for reference.

The body has a pair of vertical finger grip edges 92 and 94 thereof to facilitate the gripping and movement of the body.

A length of resilient deformable tubing 100 is positioned in the bore 24 to have an upper end 102 co-planar with inner surface 104 of the plug and a lower end 106 supported on the shoulder 44. The tubing is preferably silicone and thus fluidly connects inner chamber 110 of the chamber 10 with the bore 40 to transfer fluid from the chamber to that bore.

A plunger rod 120 is slidably accommodated within the bore 50 to have one end 122 thereof adjacent the bore 24, and the other end 124 thereof contacting the first inner surface 80 of the groove. The plunger rod 120 has a length selected so that when the end 84 of the groove is positioned in line with the bore (FIG. 5), the plunger rod end 122 is forced all the way into the bore 24 to be closely adjacent inner surface 58 of that bore, and when the end 86 of the groove is positioned in line with the bore 50 (FIG. 3), the plunger rod end 122 is all the way out of the bore 24.

When the rod 120 is forced all the way into the bore, the flexible tubing 100 is pinched off, thereby preventing fluid from flowing from the chamber 10 into the IV tubing 14. When the rod 120 is all the way out of the bore, the flexible tubing 100 is fully open, thereby permitting maximum fluid flow from the chamber 10 into the IV tubing 14.

The tubing 100 has a natural resiliency which forces the plunger rod 120 outwardly of the bore 50 when the skirt is turned appropriately in the circumferential widening direction thereof.

The rate of the fluid flow from chamber 10 is regulated by adjusting the skirt, as indicated in FIG. 4 for a mid-flow rate position. The tubing 100 is selected so that no deformation thereof remains after the plunger rod is moved from the flow occluding position toward the maximum flow position.

Indicia 150 are positioned on the skirt to indicate the flow rate which is set at each position of the skirt with respect to the chamber.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A device for controlling flow from an IV chamber to IV tubing comprising:

a hollow cylindrical body forming an IV chamber;

a plug integrally mounted on one end of said body and having an upper surface forming part of the IV chamber, said plug having a flow bore defined therethrough to be in fluid communication with the interior of said body;

a tapered IV tube connector attached to said plug and having a fluid passage defined therethrough to be axially aligned with and in fluid communication with said flow bore to receive fluid therefrom, said tube connector having a shoulder defined interiorly within said fluid passage;

a plunger rod bore defined in said plug to extend radially outward from said flow bore to the outside surface of said plug;

a plunger rod movably positioned within said plunger rod bore to be moved into and out of said flow bore transversely of said flow bore;

a flexible tube mounted within said flow bore to be contacted by said plunger rod, said flexible tube having one end thereof flush with said plug upper surface and another end thereof abutting said fluid passage shoulder and contacting the inner surface of said flow bore over the entire surface of said flow bore whereby said flexible tube is supported over the entire surface thereof except that surface area located adjacent to said plunger rod bore; and plunger rod moving means mounted on said body for moving said plunger rod into said flow bore to reduce the rate of fluid flow through said flexible tube, said plunger rod moving means including a skirt rotatably mounted on said cylindrical body to surround said plug, said skirt having a groove defined therein which is located to receive one end of said plunger rod, said groove being circumferentially crescent-shaped in transverse cross-section.

2. The device defined in claim 1 wherein said tube is naturally resilient and forces said plunger rod out of said flow bore when said skirt groove is oriented at a predetermined location with respect to said radial bore.

3. The device defined in claim 1 further including indicia on said skirt.

* * * * *